(12) United States Patent
Barbedette et al.

(10) Patent No.: US 7,280,727 B1
(45) Date of Patent: Oct. 9, 2007

(54) MICRO-WELL AND METHODS OF FABRICATING AND SELECTIVELY BLACKENING THE SAME

(75) Inventors: Loic Barbedette, Dudley, MA (US);
John Hansson, Brooklyn, CT (US);
Richard Strack, Sturbridge, MA (US);
Kevin Tabor, Webster, MA (US);
Michael Weisser, Sturbridge, MA (US)

(73) Assignee: Schott Corporation, Elmsford, NY (US)

( * ) Notice: Subject to any disclaimer, the term of this patent is extended or adjusted under 35 U.S.C. 154(b) by 0 days.

(21) Appl. No.: 10/935,541

(22) Filed: Sep. 7, 2004

Related U.S. Application Data

(60) Provisional application No. 60/500,806, filed on Sep. 5, 2003, provisional application No. 60/510,621, filed on Oct. 10, 2003.

(51) Int. Cl.
*G02B 6/04* (2006.01)
*C12M 1/34* (2006.01)
*C12M 3/00* (2006.01)

(52) U.S. Cl. ............... 385/120; 435/288.4; 435/288.7

(58) Field of Classification Search ............... 385/120; 435/288.4, 288.7
See application file for complete search history.

(56) References Cited

U.S. PATENT DOCUMENTS

| | | | | |
|---|---|---|---|---|
| 5,351,332 | A * | 9/1994 | Cook | 385/116 |
| 6,210,910 | B1 * | 4/2001 | Walt et al. | 435/7.32 |
| 6,713,309 | B1 * | 3/2004 | Anderson et al. | 436/518 |
| 2002/0039728 | A1 * | 4/2002 | Kain et al. | 435/6 |
| 2004/0129676 | A1 * | 7/2004 | Tan | 216/80 |
| 2005/0048571 | A1 * | 3/2005 | Danielson et al. | 435/7.1 |

* cited by examiner

*Primary Examiner*—Michelle Connelly-Cushwa
*Assistant Examiner*—Chris Chu
(74) *Attorney, Agent, or Firm*—Louis J. Franco; Law Office of Louis J. Franco

(57) ABSTRACT

Well plates adaptable for specimen sampling in the biological, chemical and pharmaceutical sciences are fabricated by dissolving fusedly-retained cores from the cladding material of a fused fiber plate to define a capillary plate including first and second faces and a plurality of through-voids into which fluidic samples may be deposited for analysis. Closed-bottom wells are defined by bonding one of the first and second faces to a base plate or by securing into well-sealing positions over the open ends of selected through-voids optical elements, each of which optical elements exhibits a predetermined optical property. Cladding material including reducible ions is exposed to a reduction atmosphere in order to blacken selected regions of a well plate, thereby enhancing sample analysis by reducing such disadvantageous phenomena as autofluorescence.

10 Claims, 10 Drawing Sheets

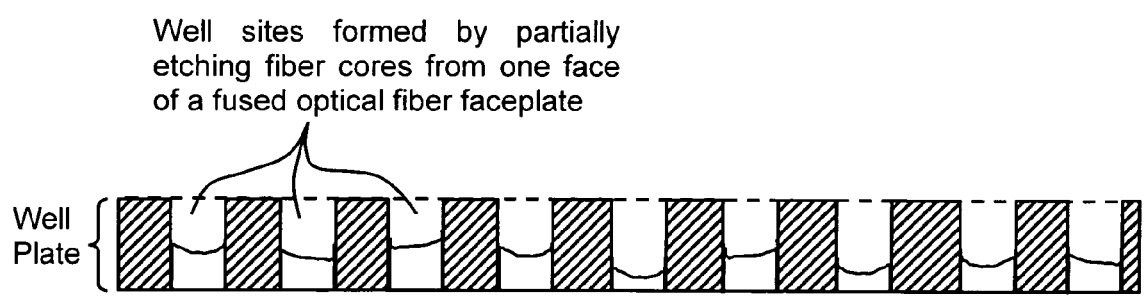
FIG. A (Background)

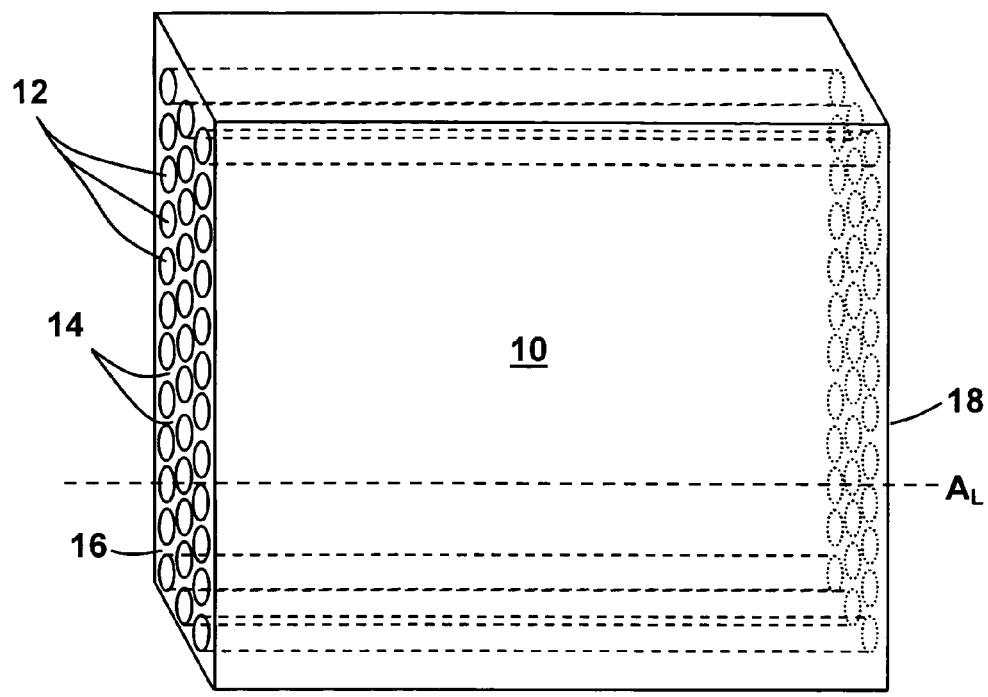
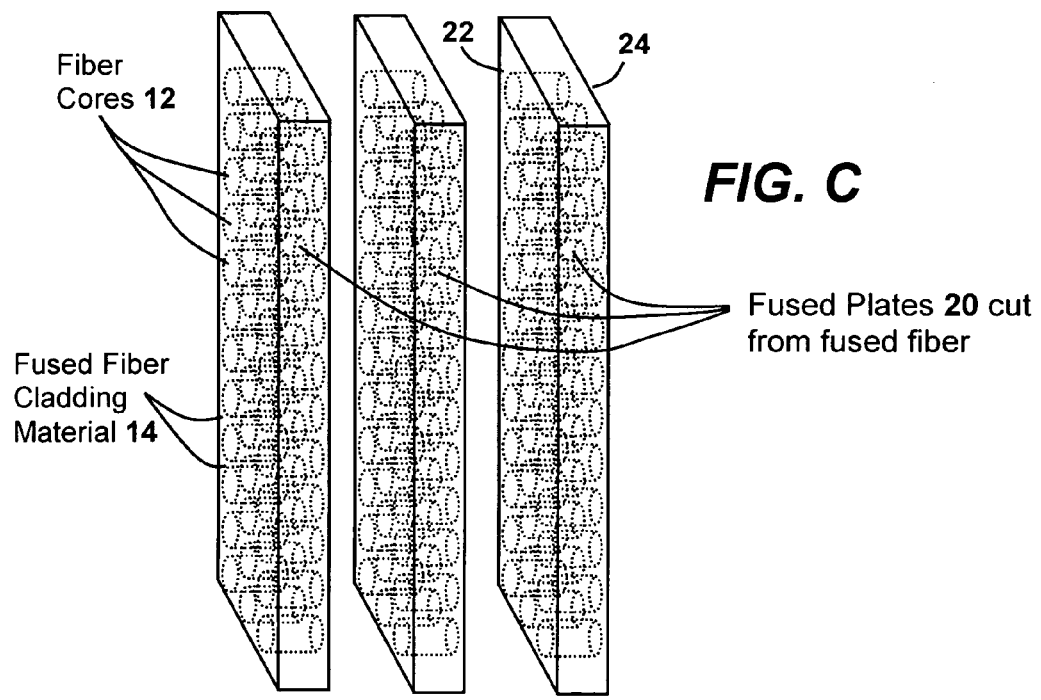

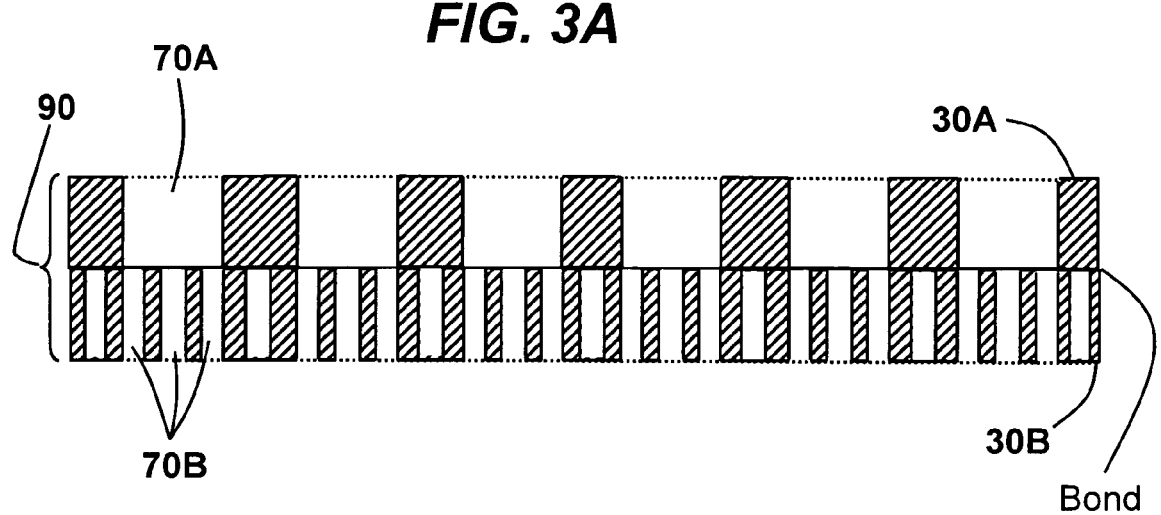
*FIG. 3A*
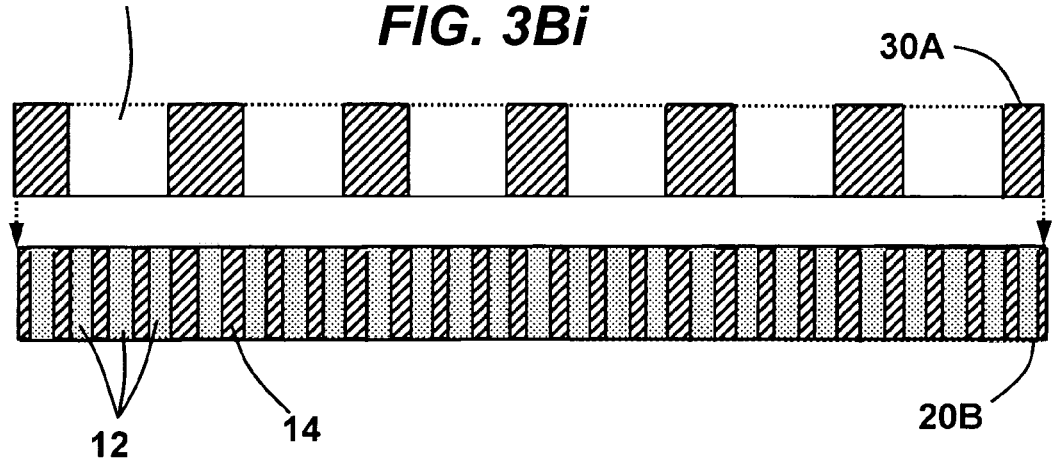
*FIG. 3Bi*
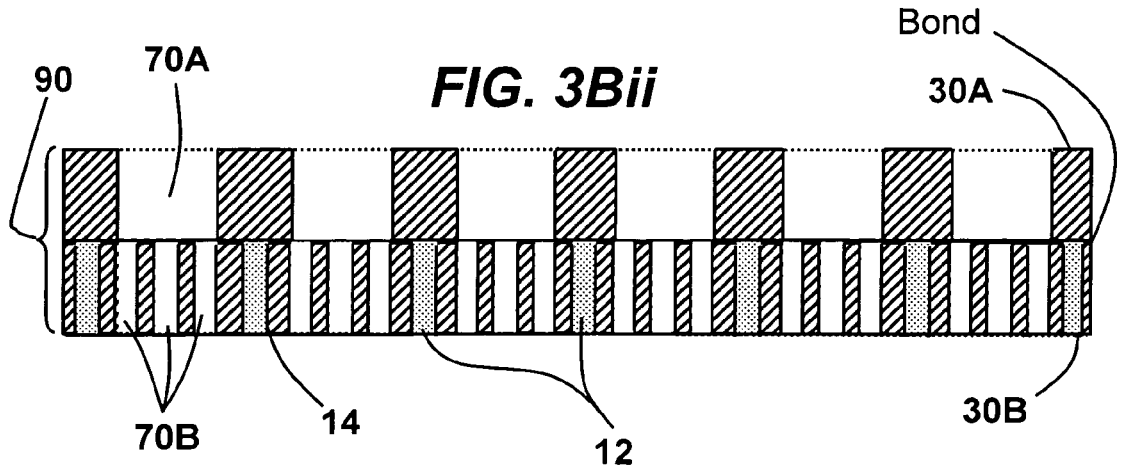
*FIG. 3Bii*

FIG. 3Biii
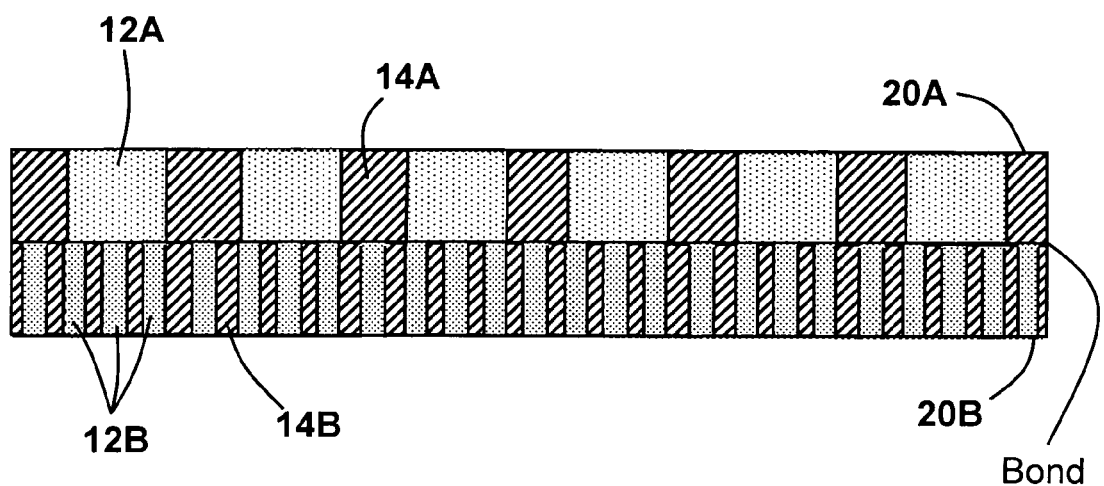
FIG. 3Biv
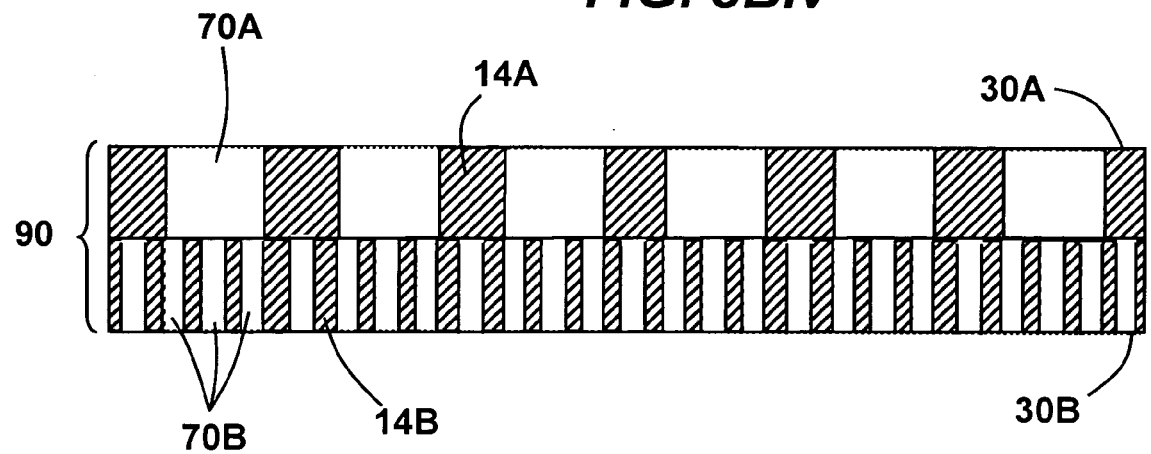

Tube of cladding material 14 including reducible ions $I_R$ (one e.g., lead $Pb^{2+}$)

End view of core 12 inserted in cladding tube 14

Reducible ions $I_R$ in cladding material 14 within walls defining voids 40.

Reduced reducible ions $I_R$ in cladding material 14 within walls defining voids 40.

Reduced reducible ions $I_R$ in cladding material 14 within walls defining voids 40 and in face 32.

MICRO-WELL AND METHODS OF FABRICATING AND SELECTIVELY BLACKENING THE SAME

PROVISIONAL PRIORITY CLAIM

Priority based on Provisional Application Ser. No. 60/500,806, filed Friday, Sep. 5, 2003, and entitled "MICRO-WELL PLATES AND METHODS OF FABRICATING THE SAME," and Provisional Application 60/510,621, filed Friday, Oct. 10, 2003, and entitled "MICRO-WELL PLATES AND METHODS OF FABRICATING AND SELECTIVELY BLACKENING THE SAME" is claimed.

BACKGROUND

Micro-well and nano-well plates, which are, in relevant industries, collectively referred to as "microtiter plates," are used widely in biological, chemical and pharmaceutical research applications for the purposes of selectively retaining and analyzing small quantities of biological and chemical agents. Currently, microtiter plates are predominantly fabricated from injection-molded and/or machined plates of plastic is formed to included multiple, well-ordered well sites. For various reasons, including analytical efficiency and conservation of valuable reagents, the pharmaceutical industry, for example, has placed increasing emphasis on miniaturized sample-screening formats. Accordingly, well-density on microtiter plates has continually increased and, for instance, a standard 3×5-inch microtiter plate currently includes 1536 holes (i.e., wells). It will be appreciated, however, that the degree to which well sites can be miniaturized in an effort to accommodate more numerous well sites on a plate of standardized dimensions is limited by conventional fabrication methods.

In response to the call for well-site miniaturization, the fiber optics industry has undertaken limited efforts to fabricate well plates by selectively intagliating optical fiber faceplates. More specifically, the state of the art in this regard is represented by a process in fabrication of a fiber optic faceplate including a plurality of cores fusedly retained by fused cladding material in accordance with standard processes well-known to those of ordinary skill in the optical-fiber-component fabrication arts. The cores are fabricated from a core material that is soluble in a predetermined solvent in which the cladding material is relatively insoluble. The faceplate is then chemically etched from one side to partially dissolve selected cores to define a set of closed-bottom wells in the fused cladding material. As illustrated by well plate of FIG. A, one limitation of the current faceplate intagliation process is the prohibitive difficulty of defining wells of uniform depth that exhibit "intended" bottom profiles. The well plate of FIG. A exhibits non-uniform well depth and irregular well bottoms, characteristics that are exaggerated for illustrative purposes.

Accordingly, in light of the limitations of traditional well-plate fabrication processes and the more nascent efforts to intagliate optical fiber faceplates for adaptation as well plates, there exists a need for improved methods of fabricating well plates exhibiting large numbers of small, well-defined and uniform well sites.

SUMMARY

Implementations of the present invention are directed to methods of fabricating micro-well plates useable for the containment and analysis of small volumes of chemical and biological materials and, in various embodiments, to micro-well plates made in accordance with the methods.

Various aspects employ techniques analogous to those applied in the fabrication of optical fiber faceplates. For instance, various implementations include the formation of a fused fiber bundle including a plurality of fused fibers extending generally along a longitudinal axis between first and second ends. Each fiber includes a core and a cladding, the core being soluble in a first solvent (e.g., an acid or base) and the cladding being relatively insoluble in the first solvent. In various aspects, each of the core and the cladding comprises glass. When individual fiber preforms, each of which comprises a cladding tube and a core bar inserted therein, are bound, heated and drawn, each cladding tube collapses and fuses around the core positioned therein and the claddings of adjacent fibers become fused to one another resulting in a unitary structure (i.e., a "fused bundle"). The formation of such structures is generally known among fabricators of fused optical fiber components.

The fused fiber bundle is cut along, but not necessarily parallel to, a plane that extends perpendicularly to its longitudinal axis to form a plurality of fused fiber plates, each of which fused fiber plates includes first and second faces. In various implementations, the first and second faces of a fused fiber plate are ground and polished to create smooth faces and, if desired, a fused plate of uniform thickness or alternative profile. The plate is exposed to the first solvent (e.g., immersed) to etch out (i.e., dissolve) the cores, thereby forming a "capillary plate" comprising the fused cladding material including a plurality of voids corresponding in position and cross-section to the pre-etch positions and cross-sectional geometries of the dissolved cores. In a typical version, the capillary plates are exposed to the first solvent for a period of time sufficient to produce a selected set of voids including "through-voids" that extend through the capillary plate between the first and second faces thereof.

In accordance with one set of implementations, a base plate of material (e.g., glass or plastic) including first and second sides is bonded to the first face of a capillary plate including through-voids to define a unitary well plate including a plurality of wells, each of which wells has an open top end, a closed bottom end and a well wall extending between the open top and closed bottom ends. Representative bonding techniques and agents for bonding the capillary and base plates include, by way of non-limiting example, (i) heat fusing, with or without frit, (ii) epoxy or other polymeric adhesive bonding agent, (iii) sol gel, (iv) laser tacking and (v) anodic bonding. Although the aforementioned bonding is performed, in some implementations, subsequent to the formation of a capillary plate, in an alternative fabrication method, the capillary plate and the base plate are bonded together prior to etching core material from the capillary plate. Alternatively configured well plates fabricated in general accordance with the foregoing methods include at least one of (i) various well sizes in the same capillary plate, (ii) clear, translucent or opaque capillary plate material, and (iii) a base plate including plurality of adjacently-bonded image conduits such as fused optical fibers (e.g., an optical fiber faceplate) including, in some versions, graded-refractive-index (i.e., GRIN) optical fibers. In addition, it will be appreciated that the wells can be randomly arranged or organized into well-ordered arrays, depending on the application for which a particular embodiment is to be used. Moreover, well size, cross-sectional geometry and diameter are variable within the same well plates by fusing into the initial fiber bundle cores of correspondingly various geometries and diameters/r dii. Although "diameter" is frequently thought of narrowly as the longest chord that can be fitted within the curve defining a circle, the more general definition of that term is applicable to this description and the appended claims. For instance, chords within squares, rectangles, hexagons, and even, irregular shapes are also diameters. A radius is a line segment extending from the geometric center of a shape to the boundary of the shape. Nothing in the preceding explanation should be construed to attribute to the terms "diameter" and "radius" a meaning more narrow than common usage and technical mathematical usage would attribute to them.

Various alternative embodiments include wells having integrated optical-focusing bottoms. Illustrative versions include a capillary plate in which each well of a selected plurality of wells is "plugged" or "capped" by a focusing element such as a ball lens, an aspheric lens or a GRIN optical fiber, by way of non-limiting example. In various such versions, the lens element serves the dual functions of providing a closed bottom for the well to which it is applied and facilitating empirical study of contents deposited in the well. Alternative versions integrate fiber segments formed from cores that are fused into the surrounding cladding material during fabrication of a fused bundle. In such a version, one of the first and second faces and of a fused fiber plate cut from the fused bundle is exposed to a core solvent for a period of time sufficient to etch away a portion, but not the entire length, of each core of a selected set of cores with the remaining, non-etched segment of each core serving as the closed bottom end of a well and, as applicable, a focusing element or a light-filtering element, for example.

In still further embodiments, the clad material defining an interior wall of each void of a selected set of voids in a capillary plate includes reducible ions (i.e., ions that can be caused to accept electrons). In various aspects, such embodiments are subjected to conditions (i.e., a reducing atmosphere) that cause reducible ions within the clad material to accept electrons (i.e., be reduced), thereby "blackening" the material. As discussed in greater detail in the detailed description, and illustrated in the drawings, the blackening of the void/well walls in various embodiments yields desirable characteristics including, but not limited to, the maintenance of a relatively low and constant level of undesirable autofluorescence over a range of light intensities and wavelengths. It should be noted that not all ions will result in blackening when such ions are reduced and, therefore, ions that result in blackening when reduced are to be selected in various implementations. Moreover, it should be noted that "blackening" is used throughout the specification and claims in a broad, informal sense and includes, for example, darkening other than strictly blackening and that may manifest itself in various shades of brown or gray by way of non-limiting example. More specifically, "blacken," "blackened" and "blackening" should be read and interpreted as broadly as "darken," "darkened," and "darkening" regardless of actual color and shade characteristics.

It will be appreciated that the cladding material can be blackened by design in any portion desired and that selective blackening is not limited to void or well walls. For example, either face of a capillary plate may be blackened in addition to, or to the exclusive of, well or void walls. Moreover, the blackening is, in various versions, performed prior or subsequent to other fabrication steps, depending on the desired result. For instance, according to three alternative methods of fabricating a well plate including a capillary plate that is at least partially blackened, a capillary plate including reducible ions is exposed to a reducing atmosphere to at least partially blacken the cladding material prior to bonding with a base plate; (ii) subsequent to bonding with a base plate and (iii) both prior and subsequent to bonding with a base plate. In other versions in which it is desired to produce a capillary plate in which just at least one of the two faces is blackened, a fused fiber plate including cladding with reducible ions is exposed to a reducing atmosphere prior to dissolving the cores therefrom.

Representative embodiments are more completely described and depicted in the following detailed description and the accompanying drawings.

BRIEF DESCRIPTION OF THE DRAWINGS

FIG. A depicts a selectively intagliated optic fiber faceplate exhibiting a plurality of well sites;

FIG. B depicts a fused fiber bundle including a plurality of cores surrounded, and retained in position, by fused cladding material;

Figure 1A:
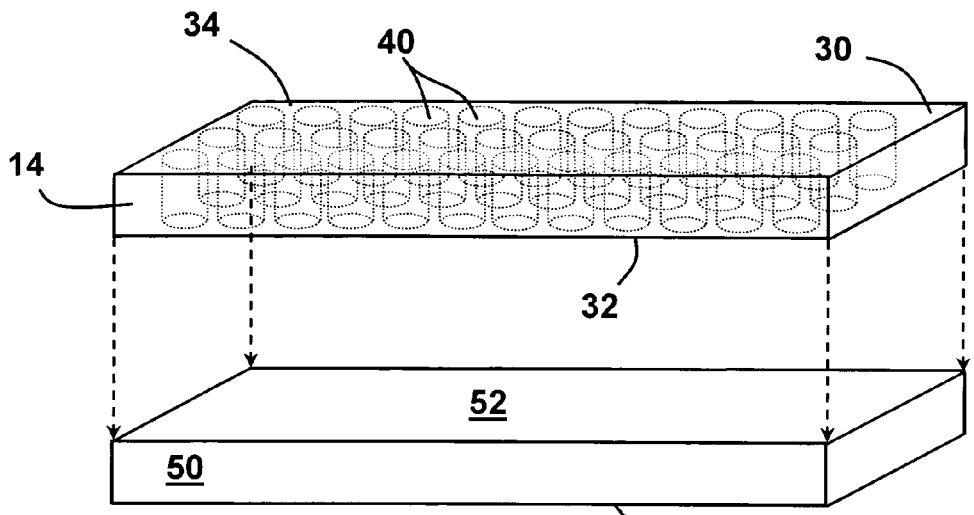
Figure 1B:
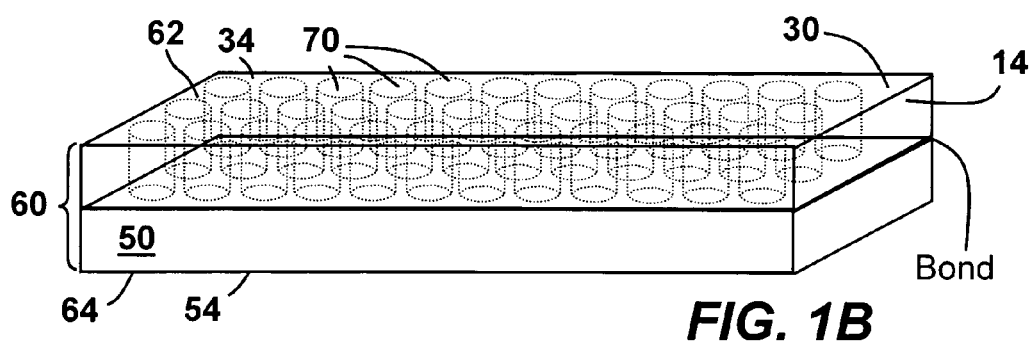
Figure 1C:
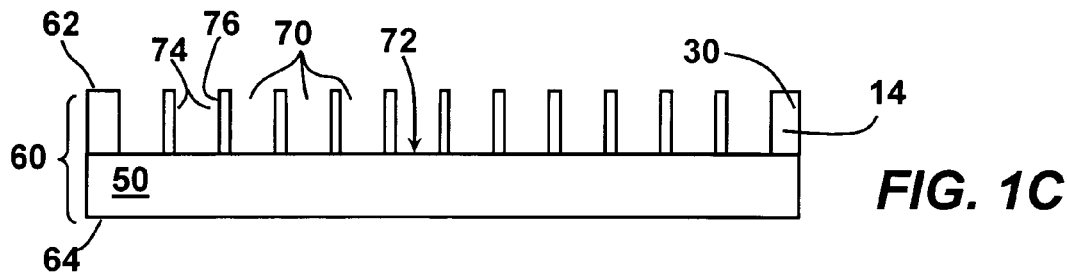
Figure 1D:
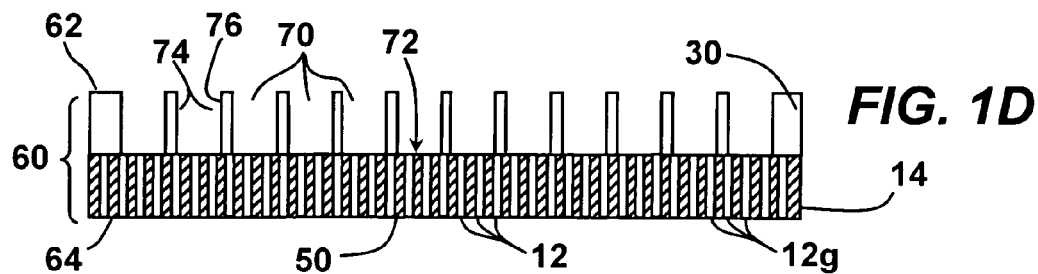
Figure 2A:
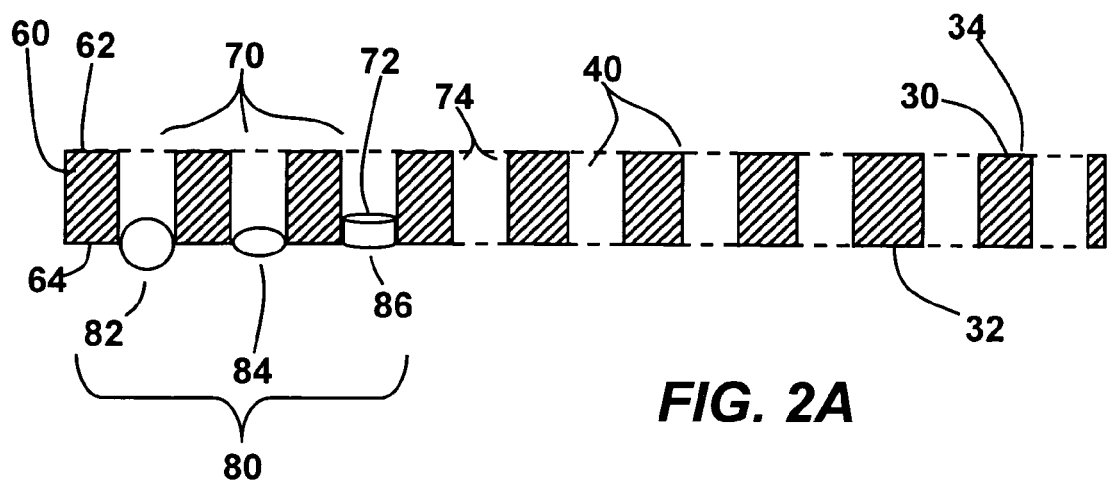
Figure 2B:
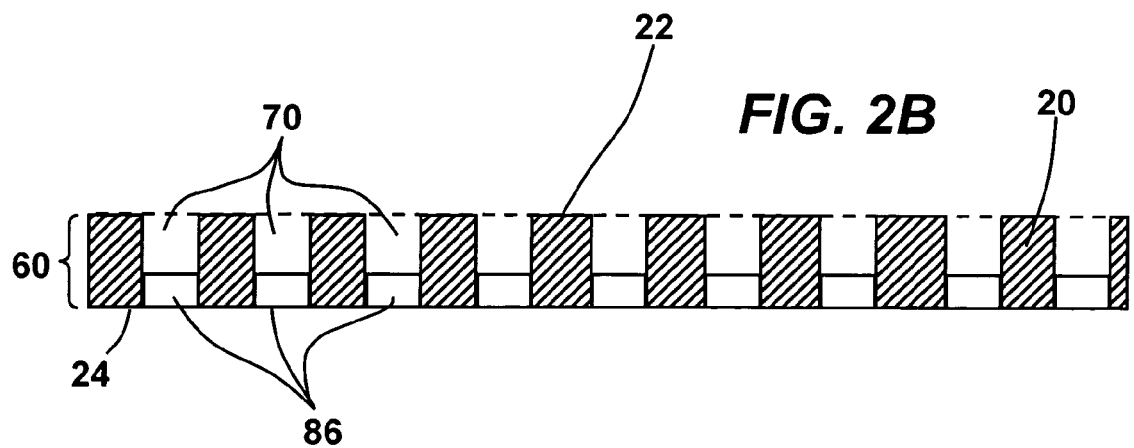
Figure 4:
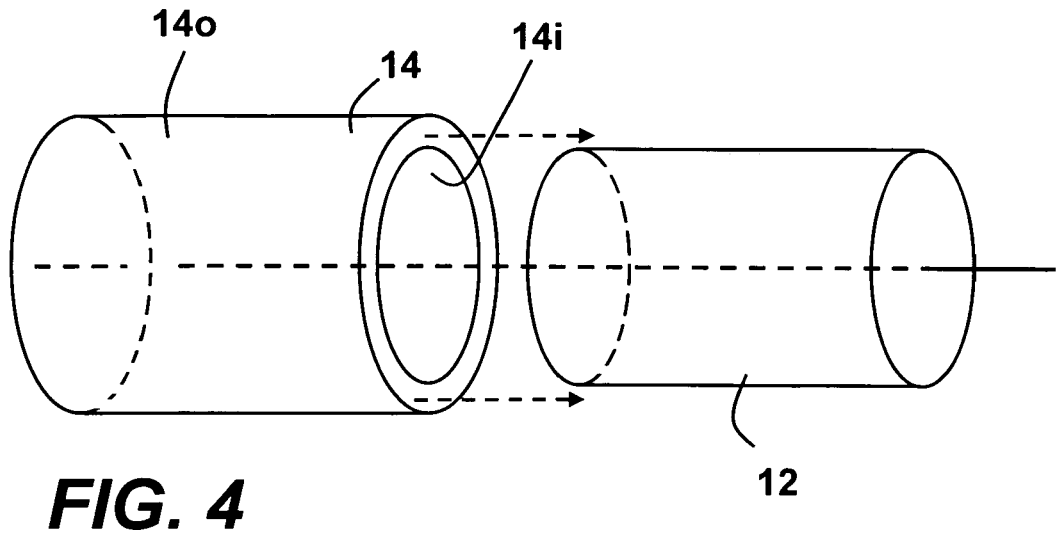
Figure 4A:
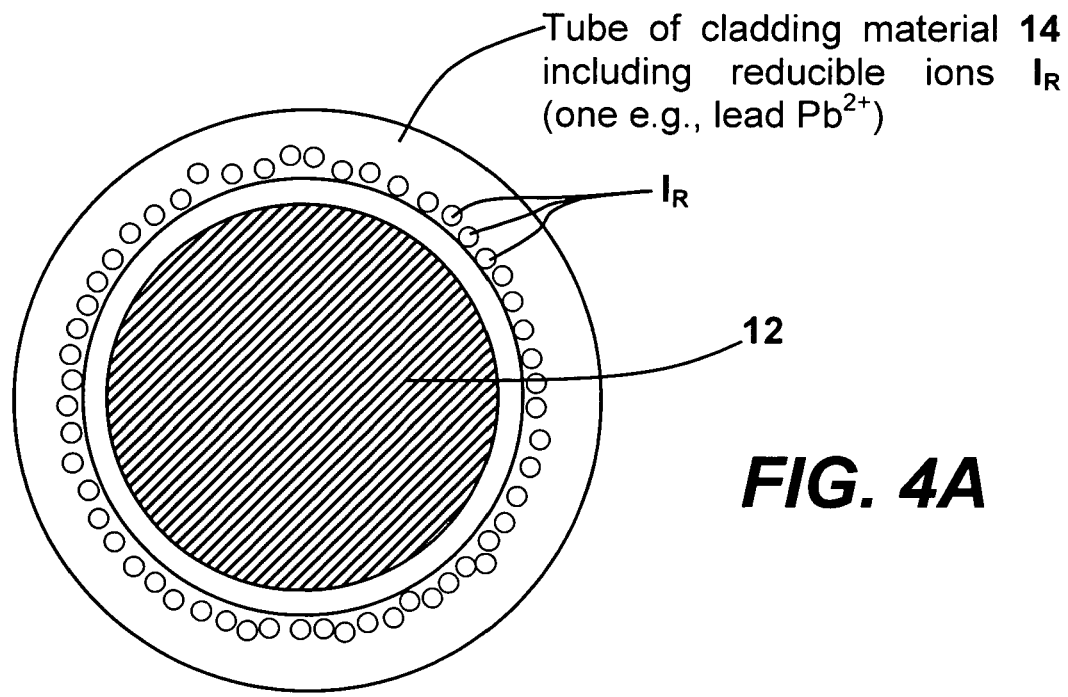
Figure 5A:
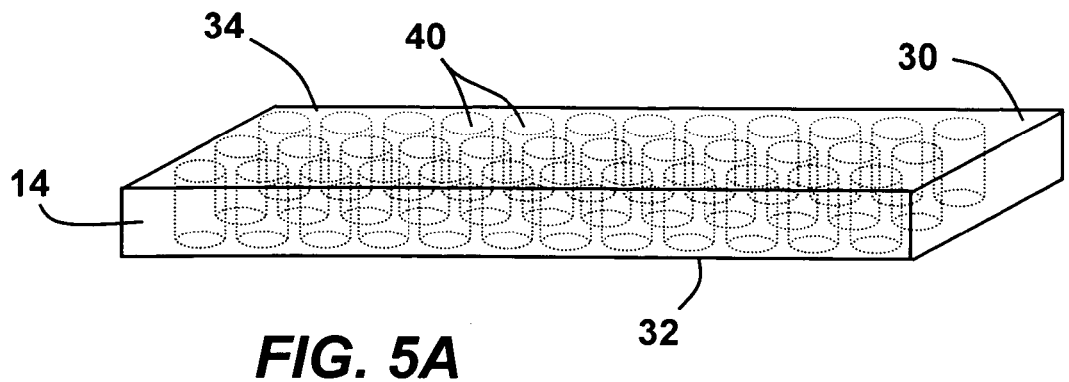
Figure 5B:
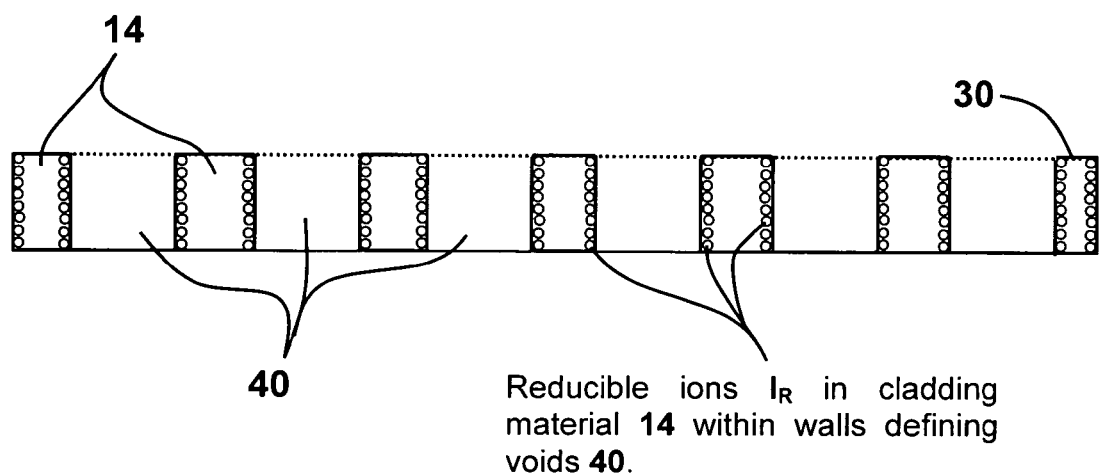
Figure 5C:
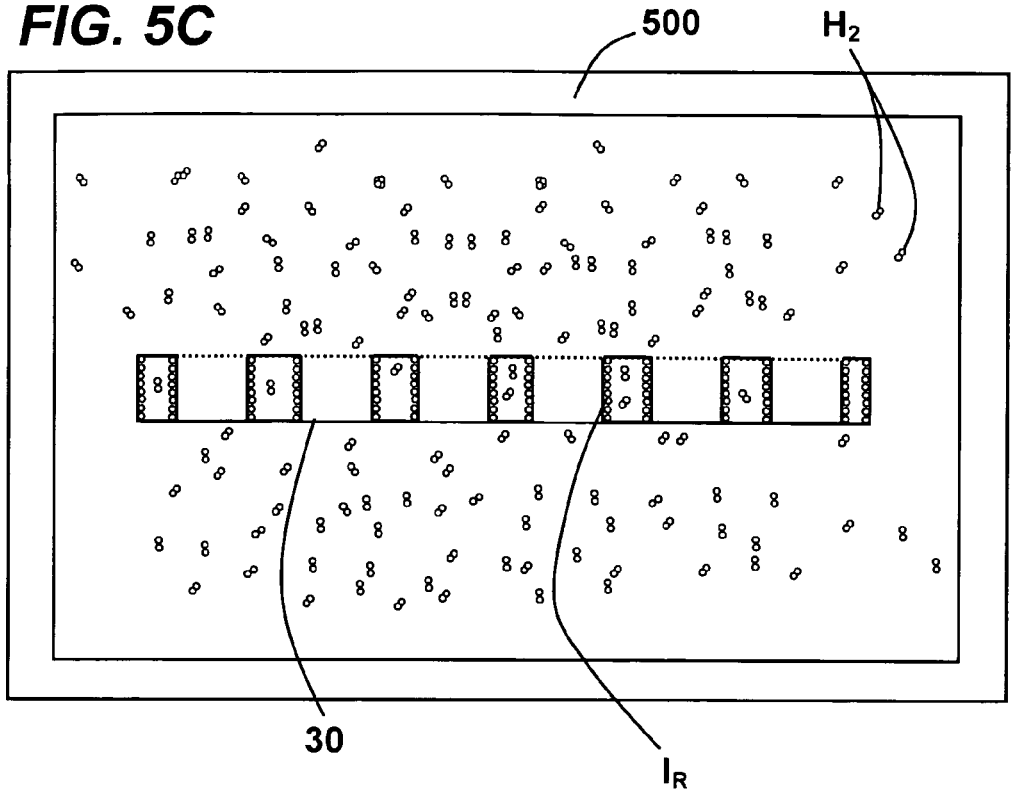
Figure 5D:
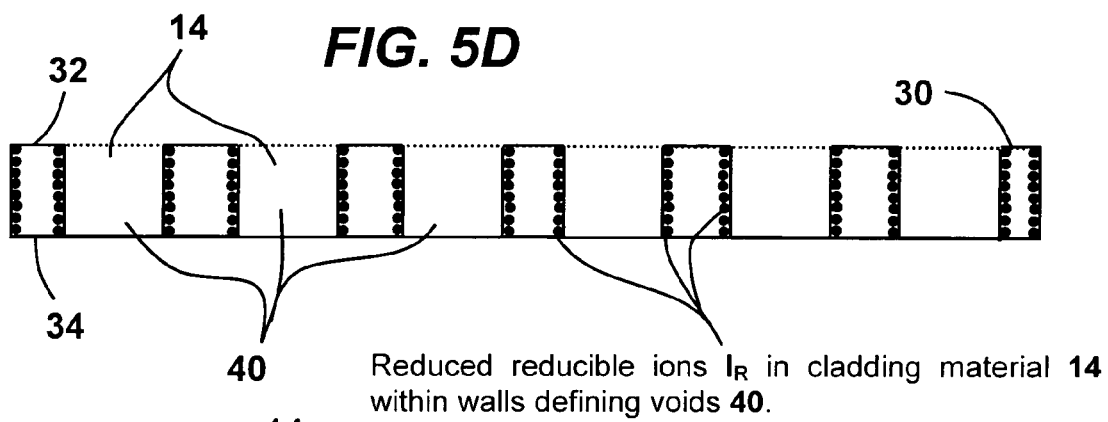
Figure 5E:
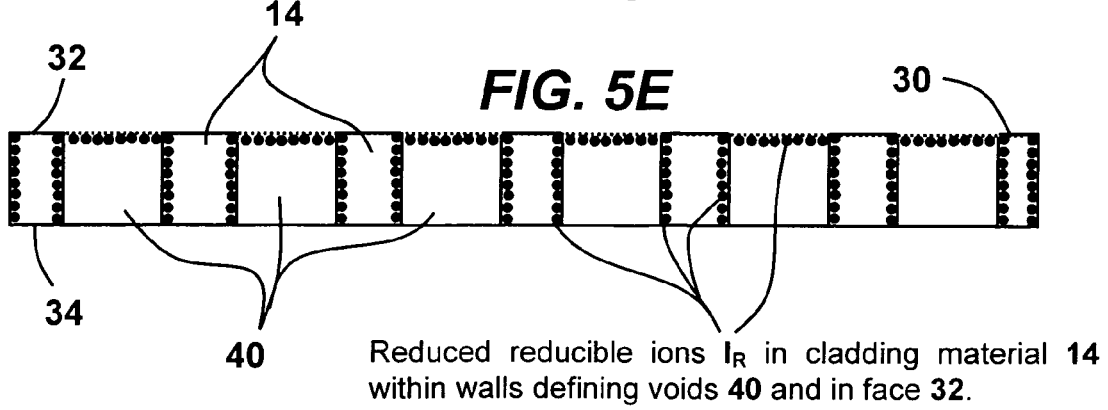
Figure 6:
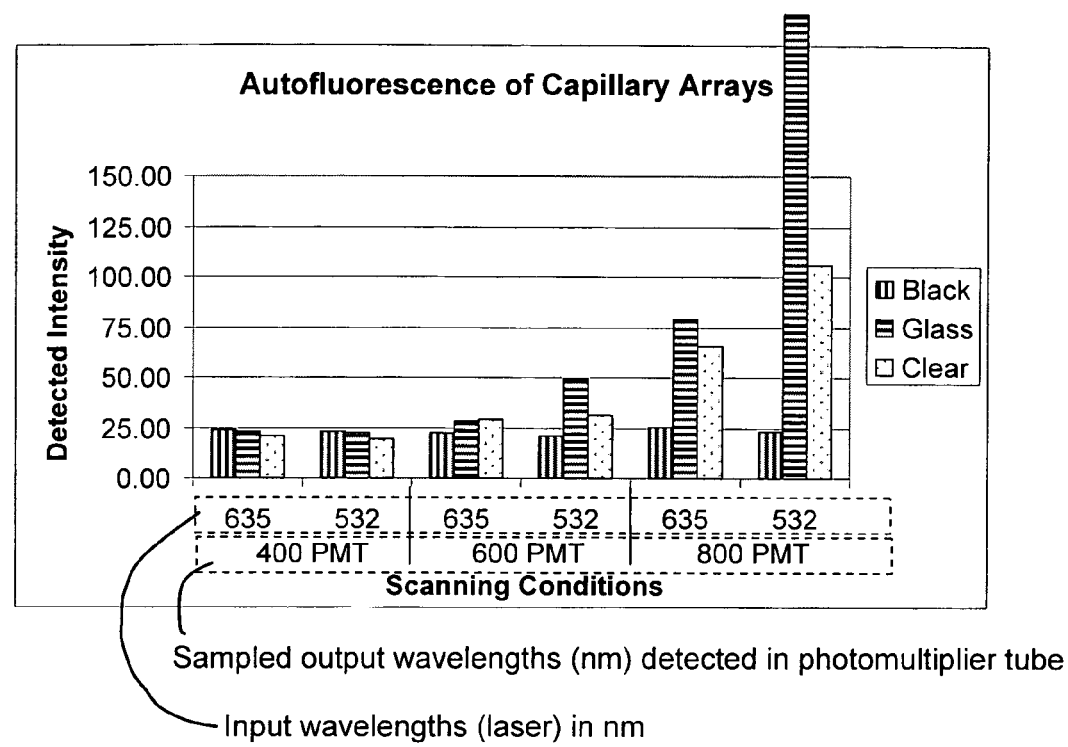

FIG. C shows fused fiber plates cut from the fused fiber bundle of FIG. B;

FIG. 1A shows a capillary plate, which includes a plurality of through-voids created by etching out cores from a fused fiber plate, being brought into contacting engagement with a base plate;

FIG. 1B shows the capillary and base plates of FIG. 1A bonded together to form a well plate;

FIG. 1C is a cross-sectional view of a well plate formed by bonding a capillary plate to a base plate;

FIG. 1D is a cross-sectional view of a well plate, such as the well plate in FIG. 1C, in which the base plate is formed from adjacently fused optical fibers;

FIG. 2A depicts an alternative well plate formed by plugging through-voids in a capillary plate with various illustrative optical-focusing elements;

FIG. 2B shows a well plate formed by the selective controlled partial etching of cores from one side of a capillary plate;

FIG. 3A shows a large-well/small-well plate having open wells in each of two adjacently bonded capillary plates wherein the wells in one capillary plate are larger in cross-sectional area than the wells of the adjacent plate;

FIGS. 3Bi and 3Bii depict two stages in the assembly of a large-well/small-well capillary plate;

FIGS. 3Biii and 3Biv depict two stages in an alternative method of fabricating a large-well/small-well capillary plate;

FIG. 4 illustrates the insertion of a glass core rod into a glass tube cladding in accordance with the "rod in tube" method of optical fiber fabrication known to those of ordinary skill in the art of the optical fiber fabrication;

FIG. 4A is an end view of an illustrative cylindrical core rod in a cylindrical tube cladding in which the cladding material includes reducible ions adjacent its inner surface;

FIG. 5A shows a fused capillary plate, including a plurality of through voids, created by etching out cores from a fused fiber plate;

FIG. 5B is a cross sectional view of a representative segment of the capillary plate of FIG. 5A showing reducible ions included in the fused fiber cladding material along the void walls;

FIG. 5C shows an illustrative capillary plate like the capillary plate of FIGS. 5A and 5B inside a hydrogen-firing furnace where it is exposed to heated gas including diatomic hydrogen to reduce reducible ions in the cladding material;

FIG. 5D shows the capillary plate of FIGS. 5A through 5C after reduction of reducible ions and the resultant void-wall blackening;

FIG. 5E shows an alternatively blackened capillary plate including blackening on the faces thereof; and FIG. 6 shows comparative autofluorescence data for (i) a blackened capillary plate, (ii) a clear (i.e., non-blackened) capillary plate and plain clear (i.e., non-blackened) glass.

DETAILED DESCRIPTION

The following description of methods of fabricating micro-well plates, and of micro-well plates fabricated in accordance therewith, is demonstrative in nature and is not intended to limit the invention or its application of uses. The various implementations, aspects, versions and embodiments described in the summary and detailed description are in the nature of non-limiting examples falling within the scope of the appended claims and do not serve to define the maximum scope of the claims.

Referring to FIGS. B and C, various implementations include one of (i) fabricating and (ii) providing a fused fiber bundle 10 including a plurality of cores 12 extending through fused cladding material 14 along a longitudinal axis $A_L$ between first and second ends 16 and 18 of the fiber bundle 10. As is generally known by those of ordinary skill in the art of optical-fiber component fabrication, a fused bundle such as the illustrative bundle 10 of FIG. B is formed by temporarily binding, and then heating and drawing, a plurality of constituent fiber preforms each of which fiber preforms includes a core bar and a cladding tube disposed around the core bar (not shown). When the bound assembly of fiber preforms is heated and drawn, each cladding tube collapses around, and fuses to, the core bar inserted therein and the cladding tubes of adjacent fiber preforms fuse to one another resulting in a unitary structure (i.e., a fused bundle 10) including a plurality of cores 12 fusedly retained within fused cladding material 14.

Referring to FIG. C, fused fiber plates 20 are formed by cutting the fused bundle 10 perpendicularly to the longitudinal axis $A_L$ thereof. Each fused fiber plate 20 has a first face 22 and a second face 24. In a typical implementation, the first and second faces 22 and 24 are ground and polished to create smooth, planar faces. However, cutting, grinding and polishing to create other-than-planar faces and plate profiles that are of other-than-uniform thickness is within the scope and contemplation of the invention.

In various implementations, the cores 12 are made from a material that is more soluble in a predetermined solvent than the fused cladding material 14 to facilitate selective chemical etching of cores 12 from the fused cladding material 14. When at least a portion of the fused fiber plate 20 is exposed to the predetermined solvent for a sufficient length of time, cores 12 are etched out of the fused cladding material 14 resulting in a capillary plate 30 such as the illustrative capillary plate shown in FIG. 1A. The capillary plate 30 of FIG. 1A has first and second faces 32 and 34 and comprises the fused cladding material 14 and a plurality of voids 40 corresponding in position and cross-sectional geometries to the pre-etch positions and cross-sections of the cores 12 dissolved out of the fused fiber plate 20. The voids 40 in the illustrative capillary plate 30 of FIG. 1A are referred to as "through-voids" because they extend through the capillary plate 30 between the first and second faces 32 and 34.

FIGS. 1A through 1C depict the fabrication of a well plate 60 incorporating the illustrative capillary plate 30 and a base plate 50. The base plate 50 is, for example, a planar plate of glass including first and second sides 52 and 54. The first face 32 of the capillary plate 30 is bonded to the first side 52 of the base plate 50 to form a well plate 60 including an upper side 62, a lower side 64 and a plurality of wells 70, each of which wells 70 has a closed bottom end 72, an open top end 74 and a well wall 76 extending between the open closed bottom and open top ends 72 and 74. Depending on the types of analyses to be performed on materials deposited into the wells 70, the base plate 50 can alternatively exhibit at least one optical attribute of a selected set of optical properties including, for example, (i) transparency, (ii) translucency, (iii) selective electromagnetic wavelength filtration, (iv) electromagnetic wavelength polarization, (v) dispersion, (vi) image focus, (vii) image magnification and (viii) image reduction. In various alternative embodiments, a base plate 50 fabricated from fused optical fibers facilitates one or more of the aforementioned attributes. For instance, in some versions, selective light filtration is achieved by the use of doped or tinted core glass in a fused fiber base plate 50. In another instance, base-plate focusing properties are achieved by fusing GRIN optical fibers to form the base plate 50. FIG. 1D depicts a version of a well plate 60 in which the base plate 50 is comprised of adjacently fused optical fibers that may, in alternative versions, include at least one of tinted cores 12 and cores 12g exhibiting graded refractive index profiles retained by fused cladding material 14. For the sake of simplicity, and in accordance with conventional industry terminology, cores 12g that are fusedly retained in a faceplate, and that exhibit graded-refractive-index profiles, are alternatively referred to as GRIN fibers or, where appropriate, GRIN fiber segments. The incorporation of GRIN fibers in the base plate 50, in alternative implementations, facilitates at least one of (i) the focused illumination of fluidic samples (not shown) contained in the wells 70 from the second side 54 of the base plate 50 and (ii) the observation of samples in the wells 70 through the second side 54 of the base plate 50.

Referring to FIG. 2A, an alternatively configured well plate 60 includes wells 70 having integrated optical-focusing closed bottom ends 72. The well plate 60 of FIG. 2A comprises a capillary plate 30 wherein each void 40 of a selected plurality of voids 40 is closed by a focusing element 80 to form a well 70. In the illustrative example of FIG. 2A, one example of each of a ball lens 82, an aspheric lens 84 and a GRIN optical fiber segment 86 is shown defining the closed bottom end 72 of a well 70. In alternative embodiments, focusing elements 80 are secured into a well-sealing position by, for example, at least one of press fitting, fusing, epoxy or other adhesive bonding agent, laser tacking and anodic bonding. In addition to sealing the void 60 over which it is applied, a focusing element 80 facilitates empirical study of contents deposited in the well 70 for analysis.

Each illustrative focusing element 80 of FIG. 2A is positioned over one end of a through-void 40 after fabrication of a capillary plate 30 and then secured in place. Distinguishably, the well plate 60 of FIG. 2B includes integrated GRIN fiber segments 86 formed from cores 12 that are fused into the surrounding cladding material 14 during fabrication of a fused bundle 10. One of the first and second faces 22 and 24 of a fused plate 20 cut from the bundle 10 is exposed to a core solvent for a period of time sufficient to etch away (dissolve) a portion, but not the entire length, of each core 12 of a selected set of cores 12 such that the remaining, non-etched segment 86 of each core 12 does not extend the full distance by which the first and second faces 22 and 24 are separated and is, therefore, recessed with respect to the etched face 22 or 24 and serves as the closed bottom end 72 of a well 70 and as a focusing element 80. The depth and volume of a well 70 is controllable by regulating the exposure time of the core 12 to the solvent. It will be appreciated that a well plate 60 having wells 70 of various predetermined depths can be formed by, for example, selective masking and exposure of cores 12 and that the fused plate 20 can, in various implementations, be etched from either or both of the first and second faces 22 and 24. Moreover, well volume is a function of cross-sectional geometry and diameter of the cores 12 initially present in a fused plate 20 and, in various embodiments, cores 12 of various geometries and diameters are incorporated into the same fused plate 20.

Referring to FIG. 3A, a large-well/small-well plate 90 includes a first capillary plate 30A bonded to a second capillary plate 30B. Each of the first and second capillary plates 30A and 30B includes wells 70 that are open at either end. That is, they are through-voids 40 extend through the capillary plate 30. Moreover, in the illustrative example, each well 70A of a selected set of wells 70A within the first capillary plate 30A is in fluid communication with a plurality (at least two) smaller wells 70B within the second capillary plate 30B. In one alternative version, a large-well/small-well plate 90 is fabricated by bonding a first capillary plate 30A to a second capillary plate 30B after the capillary plates 30A and 30B have been independently fabricated. There exists a statistical probability that such a version will include small wells 70B that are not aligned (not in fluid communication) with a larger well 70A when the two plates 30A and 30B are brought together, as shown in the large-well/small well plate 90 of FIG. 3A. Accordingly, referring to FIGS. 3Bi and 3Bii, when it is desired that each small well 70B align with a larger well 70A, an alternative implementation calls for etching the cores 12 from a first fused plate 20, such as those shown in FIG. C, to form a first capillary plate 30A and then bonding the resulting capillary plate 30A to a non-etched second fused plate 20B including cores 12 smaller in cross-sectional area than the through-voids 40 in the first capillary plate 30A. A core solvent (not shown) is then introduced into the larger wells 70A of the first capillary plate 30A to etch out cores 12 in the second fused plate 20B only where cores 12 in the second fused plate 20B are aligned with large wells 70A thereby forming the second capillary plate 30B including wells 70B. Cores 12 in the second capillary plate 30B that are not aligned with a larger well 70A in the first capillary plate 30A remain fused within the second capillary plate 30B. In still another implementation, a large-well/small-well plate 90 is fabricated by bonding a first fused fiber plate 20A to a second fused fiber plate 20B and then exposing the bonded plates 20A and 20B to a core solvent (not shown) in order to etch out the cores 12A and 12B from, respectively, fused fiber plates 20A and 20B and form the capillary plates 30A and 30B as shown in FIGS. 3Biii and 3Biv. In the particular version of FIGS. 3Biii and 3Biv, the first fused fiber plate 20A includes cores 12A that are larger in cross-section than cores 12B in fused fiber plate 20B. Accordingly, subsequent to core dissolution, the wells 70A in capillary plate 30A are larger in cross-section than the wells 70B in the capillary plate 30B.

Large-well/small-well plates 90 are alternatively useable as filters elements. They are also adaptable for use in the study of materials in liquid form that are retained by capillary forces in the small wells 70B of the second capillary plate 30B. The large wells 70A facilitate cleaning of the small wells 70B by the introduction of, for example, water or a cleaning solution through the large wells 70A to displace material from the small wells 70B.

As stated in the summary, various versions include voids 40/wells 70 defined by blackened cladding material 14. An illustrative method of fabricating a capillary plate 30 including voids 40 defined by blackened cladding material 14 is explained in general terms in conjunction with FIGS. 4 through 5D. It is to be understood that such capillary plates 30 can be used in the fabrication of any of the various illustrative well plates described above through the execution of variously combined blackening steps described herein and fabrication steps described above. Moreover, as with the non-blackened embodiments described above, some of the details of the standard rod-in-tube, and bundling and fusing, methods of fabricating fused bundles and faceplates are not provided because they are established methods known to those of ordinary skill in the optical fiber fabrication arts.

Referring to FIGS. 4 and 4A, various implementations include insertion of a core 12 into a tube of cladding material 14 having inner and outer surfaces 14i and 14o that includes a plurality of reducible ions $I_R$ at least adjacent the inner surface 14i of the cladding material 14. A fused fiber bundle 10 is then formed using multiple, adjacently bound fibers in accordance with the method previously described for non-blackened versions and shown in FIGS. B and C. The bundle 10 is then cut to form one or more fused plates 20, as previously discussed, and cores 12 are selectively etched therefrom to form a capillary plate 30 having a plurality of voids 40 defined by walls of cladding material 14 including reducible ions $I_R$ as shown in FIG. 5A and the cross-sectional view of FIG. 5B.

Referring to FIG. 5C, the capillary plate 30 is then placed into a reducing atmosphere such as hydrogen-firing furnace 500 where it is exposed to heated hydrogen gas $H_2$ for a predetermined length of time. At a predetermined temperature falling within a predetermined temperature range, the di-atomic hydrogen $H_2$ reduces reducible ions $I_R$ in the cladding material 14 defining voids 40. The reduction of the reducible ions $I_R$ results in the blackening of the cladding material 14, as shown in FIG. 5D, which, as discussed briefly in the summary, yields advantageous autofluorescence-negating characteristics to the capillary plate 30. The length of time and temperature ranges required to achieve desired results depend on such factors as (i) the type of glass used as cladding material 14, (ii) the nature of the reducible ions $I_R$, and (iii) the concentration of diatomic hydrogen $H_2$ present in the furnace 500. One illustrative successful method executed by the inventors exposed a capillary plate 30 to hydrogen $H_2$ for 12 hours at 450° C. Also variable are the inner diameters and cross-sectional geometries of the voids 40, the thickness of the capillary plate 30 and the surface area and configuration of the capillary plate 30. For instance, depending on intended usage, voids 40 having diameters of anywhere from 10 microns to 1000 microns are advantageous, although this range by no means constitutes a limit on the scope of the invention.

In the illustrative example of FIGS. 4 through 5D, tubes of cladding material 14 having reducible ions $I_R$ only in the vicinity of the inner surface 14i thereof were used. Accordingly, blackening was restricted primarily to those portions of cladding material 14 defining the walls of voids 40. It will be appreciated that when tubes of cladding material 14 having reducible ions $I_R$ present throughout the tube are used, the first and second faces 32 and 34 of the capillary plate 30 may also be subject to blackening, as in the illustrative version of FIG. 5E. More generally, wherever the cladding material 14 includes reducible ions $I_R$ that are exposed to heated hydrogen gas during hydrogen firing, that portion of the cladding material 14 can be caused to blacken. Accordingly, if, for example, tubes of cladding material 14 having reducible ions $I_R$ throughout are used, and it is not desired that the faces 32 and 34 be blackened, the capillary plate 30 can be hydrogen fired and then the plate 30 can be ground and/or polished to remove blackened face material.

FIG. 6 shows illustrative comparative autofluorescence data for (i) a blackened capillary plate, (ii) a clear (i.e., non-blackened) capillary plate and a plain clear (i.e., non-blackened) glass plate. The chart includes autofluorescence intensity data at three different output wavelengths (i.e., 400, 600 and 800 nanometers) for each of two input wavelengths (i.e., 635 and 532 nanometers). For instance, the intensities of autofluorescence at 400 nm for the 532 nm input light is relatively even for the blackened capillary plate, the plate glass and the non-blackened (i.e., "clear") capillary plate. However, the intensities of autofluorescence at 800 nm corresponding to the blackened capillary plate, the plate glass and the non-blackened (i.e., "clear") capillary plate are dramatically disparate for 532 nm input light. More specifically, while the autofluorescence intensity for the blackened capillary plate 30 is relatively unchanged over all three output wavelengths (i.e., 400, 600 and 800 nm), the autofluorescence intensity at 800 nm of the clear capillary plate is over 4× the value it is at 400 nm. The steady, ascertainable value of autofluorescence intensity over a large wavelength range is a desirable attribute of blackened capillary plates 30 in part because it provides a relative "noise" constant that can be made known to users of the blackened capillary plates 30 and because it provides a much lower signal to noise ratio at higher wavelengths than the dramatically increased autofluorescence characteristic of the non-blackened capillary plates.

The foregoing is considered to be illustrative of the principles of the invention. Furthermore, since numerous modifications and changes will readily occur to those skilled in the art, it is not desired that the foregoing limit the invention to the exact construction and operation shown and described. Accordingly, all suitable modifications and equivalents may be resorted to that appropriately fall within the scope of the invention as expressed in the appended claims.

What is claimed is:

1. A method of fabricating a well plate comprising:
    fabricating a fused fiber bundle including a plurality of adjacently fused fibers extending generally along a longitudinal axis, each fiber including a core and cladding material collapsed and fused about the core, the core being soluble in a core solvent in which the cladding material is relatively insoluble;
    cutting the fused fiber bundle along a plane that extends perpendicularly to the longitudinal axis to form a fused fiber plate having opposed first and second faces;
    exposing the fused fiber plate to the core solvent in order to dissolve each core of a selected set of cores and form a capillary plate comprising fused cladding material including a plurality of through-voids extending through the capillary plate between the first and second faces and corresponding in position and cross-sectional geometry to the pre-etch positions and cross-sectional geometries of the dissolved cores;
    providing a base plate including first and second sides; and
    bonding one side of the base plate one of (i) to the first face of the fused fiber plate prior to dissolving cores from the fiber plate and (ii) to the first face of the capillary plate subsequent to the formation thereof in order to define a unitary well plate including a plurality of wells each of which wells is defined by an open top end, a closed bottom end and a well wall comprised of cladding material and extending between the open top and closed bottom ends,
    wherein the base plate is a fused fiber optic faceplate comprising a plurality of adjacently-bonded optical fiber image conduits.

2. The method of claim 1 wherein the fused bundle is cut parallel to the plane that extends perpendicularly to the longitudinal axis such that the through-voids extend generally perpendicularly to at least one of the first and second faces.

3. The method of claim 1 wherein at least a portion of the cladding material includes reducible ions and the method further comprises exposing the capillary plate to a reducing atmosphere in order to reduce at least a portion of the reducible ions in the cladding material and thereby at least partially blacken the cladding material one of (i) prior to bonding with the base plate and (ii) subsequent to bonding with the base plate such that, when the capillary plate is bonded to the base plate and the at least partial blackening has occurred, a well plate is formed that includes a set of wells each of which wells is defined by a well wall that is at least partially blackened.

4. The method of claim 1 wherein the adjacently-bonded optical fiber image conduits of the base plate include graded-refractive-index optical fibers.

5. A well plate fabricated in accordance with the method of claim 1.

6. The well plate of claim 5 wherein the adjacently-bonded optical fiber image conduits of the base plate include graded-refractive-index optical fibers.

7. A well plate comprising:
    a capillary plate having opposed first and second faces and a plurality of through-voids extending through the capillary plate between the first and second faces; and
    a fused fiber optic faceplate having opposed first and second sides and a plurality of adjacently-bonded optical fiber image conduits extending between the first and second sides,
    wherein one side of the fused fiber optic faceplate is permanently bonded to the first face of the capillary plate in order to define a unitary well plate including a plurality of wells each of which wells is defined by an open top end, a closed bottom end and a well wall extending between the open top and closed bottom ends.

8. The well plate of claim 7 wherein included among the plurality of adjacently-bonded optical fiber image conduits is at least one graded-refractive-index optical fiber.

9. The well plate of claim 8 wherein the capillary plate comprises a material including reducible ions and the capillary plate has been at least partially blackened by exposure to a reducing atmosphere of reducible ions contained therein.

10. The well plate of claim 7 wherein the capillary plate comprises a material including reducible ions and the capillary plate has been at least partially blackened by exposure to a reducing atmosphere of reducible ions contained therein.

* * * * *